United States Patent
Goetz et al.

(10) Patent No.: US 8,195,294 B2
(45) Date of Patent: Jun. 5, 2012

(54) MULTI-STAGE TESTING OF ELECTRODES OF IMPLANTABLE MEDICAL DEVICE, SYSTEM AND METHOD

(75) Inventors: Steven M. Goetz, Brooklyn Center, MN (US); Todd V. Smith, Shoreview, MN (US); Nathan A. Torgerson, Andover, MN (US); Warren W. Ball, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 625 days.

(21) Appl. No.: 12/112,460

(22) Filed: Apr. 30, 2008

(65) Prior Publication Data

US 2009/0276007 A1    Nov. 5, 2009

(51) Int. Cl.
*A61N 1/05* (2006.01)

(52) U.S. Cl. .......................................... 607/27; 607/28

(58) Field of Classification Search .................. 600/574; 607/27–29, 37
See application file for complete search history.

(56) References Cited

U.S. PATENT DOCUMENTS

| | | | |
|---|---|---|---|
| 4,870,341 A | 9/1989 | Pihl et al. | |
| 5,076,272 A * | 12/1991 | Ferek-Petric | 607/28 |
| 5,320,643 A * | 6/1994 | Roline et al. | 607/28 |
| 5,487,755 A | 1/1996 | Snell et al. | |
| 5,549,654 A | 8/1996 | Powell | |
| 5,713,937 A | 2/1998 | Nappholz et al. | |
| 5,724,985 A | 3/1998 | Snell et al. | |
| 5,891,179 A | 4/1999 | Er et al. | |
| 6,101,415 A | 8/2000 | Er et al. | |
| 6,308,100 B1 | 10/2001 | Er et al. | |
| 6,374,139 B1 | 4/2002 | Er et al. | |
| 6,721,600 B2 | 4/2004 | Jorgenson et al. | |
| 6,748,274 B2 | 6/2004 | Levine et al. | |
| 6,842,644 B2 | 1/2005 | Anderson et al. | |
| 2002/0077669 A1 | 6/2002 | Lindh et al. | |
| 2002/0120307 A1 | 8/2002 | Jorgenson et al. | |
| 2003/0088289 A1 | 5/2003 | Levine et al. | |
| 2003/0114899 A1 | 6/2003 | Woods et al. | |
| 2003/0176899 A1 | 9/2003 | Samuelsson et al. | |
| 2004/0082980 A1 | 4/2004 | Mouine et al. | |
| 2004/0098063 A1 | 5/2004 | Goetz | |
| 2004/0143303 A1 | 7/2004 | Sieracki | |

(Continued)

FOREIGN PATENT DOCUMENTS

WO    WO 9819738 A1    5/1998

(Continued)

OTHER PUBLICATIONS

International Search Report for PCT/US2009/030961.

*Primary Examiner* — Carl H Layno
*Assistant Examiner* — Paula J Stice
(74) *Attorney, Agent, or Firm* — IPLM Group, P.A.

(57) ABSTRACT

Method, controller and system for an implantable medical device capable of delivering therapeutic stimulation through a plurality of electrodes. A control module is operable to conduct a plurality of measurements of impedance values creating a plurality of measured impedance values for a plurality of selected sets of individual ones of the plurality of electrodes based on a plurality of active parameters. The control module conducts the plurality of measurements of impedance values in a plurality of stages in which at least one of said plurality of active parameters is varied between individual ones of the plurality of stages.

28 Claims, 7 Drawing Sheets

U.S. PATENT DOCUMENTS

| | | |
|---|---|---|
| 2004/0225337 A1 | 11/2004 | Housworth et al. |
| 2005/0010258 A1 | 1/2005 | Peterson et al. |
| 2005/0033385 A1 | 2/2005 | Peterson et al. |
| 2005/0107841 A1 | 5/2005 | Meadows et al. |
| 2006/0036186 A1 | 2/2006 | Goetz et al. |
| 2006/0135886 A1* | 6/2006 | Lippert et al. ............... 600/547 |
| 2006/0265024 A1* | 11/2006 | Goetz et al. ................. 607/48 |
| 2007/0255319 A1 | 11/2007 | Greenberg et al. |

FOREIGN PATENT DOCUMENTS

| | | |
|---|---|---|
| WO | WO 0143821 A1 | 6/2001 |
| WO | WO 03077992 A1 | 9/2003 |
| WO | WO 2005068017 A1 | 7/2005 |
| WO | WO 2006017277 A2 | 2/2006 |
| WO | WO 2007112061 A2 | 10/2007 |
| WO | WO 2007112061 A3 | 10/2007 |
| WO | WO 2008054438 A1 | 1/2008 |

* cited by examiner

MULTI-STAGE TESTING OF ELECTRODES OF IMPLANTABLE MEDICAL DEVICE, SYSTEM AND METHOD

FIELD

The present invention relates generally to controllers, systems and methods for implantable medical devices and, more particularly, to such controllers, systems and methods for implantable medical devices having therapeutic electrodes.

BACKGROUND

The medical device industry produces a wide variety of electronic devices for treating patient medical conditions. Depending upon medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers and defibrillators.

Implantable medical devices configured to deliver therapeutic electrical stimulation commonly deliver therapy via electrodes positioned on one or more leads operatively connected to the implantable medical device. In some instances, the housing of the implantable medical device may also serve as an electrode or an electrode may be positioned on the housing. The electrode or electrodes are commonly positioned in the patient's body during the same surgical procedure in which the implantable medical device is implanted.

The positioning of electrodes, and associated leads, is often an inexact procedure and may commonly be dependent on the particular physiologic characteristics of the patient. In addition, electrodes may commonly be positioned within the patient without the medical professional or user conducting the procedure being capable of actually seeing where the electrodes are positioned. Instead, external aides such as fluoroscopes and/or endoscopes may commonly be employed to inform the medical professional or other user as to an approximate location of the electrodes.

Due to the inherent uncertainty involved in the placement of electrodes for an implantable medical device, implantable medical devices and the external controllers that interface with the devices are commonly operable to perform a test on the leads and electrodes to verify that the leads and electrodes are functioning properly and are positioned correctly. A common test is to check the impedance between pairs of electrodes. During testing, an electrode can be driven with a signal having known electrical characteristics. The signal may be measured, e.g., on another electrode, and the impedance computed between electrodes using known fundamental relationships. The measured impedance value can give a medical professional or other user information relating to whether the electrodes involved in the test are positioned correctly and operating properly.

An external controller, or physician programmer, is commonly utilized in lead impedance tests. Physician programmers can be similar in size and composition to a large laptop computer. The physician programmer provides a user interface via a display screen, and is manipulated by a medical professional via a variety of inputs, such as buttons and touchscreens. The physician programmer commonly communicates with the implantable medical device via inductive telemetry. In order to accomplish this, a coil, operatively coupled to the controller, typically by a wire, is placed over a coil operatively coupled to the electronics in the implantable medical device, thereby establishing an inductive link over which data may be passed in either direction. Because physician programmers are typically not sterilized, the physician programmer itself is placed outside of the sterile field, only the coil and its housing is taken inside the sterile field, e.g., using a sterile bag.

For example, United States Patent Application Publication No. 2006/0036186, Goetz et al, Automatic Impedance Measurement of an Implantable Medical Device, discloses a method and controller for automating impedance measurements. An entry for each electrode pair is displayed on a user interface. Each electrode pair entry includes an identification of electrodes for an electrode pair, an associated value of impedance, and a value of current that is measured between the electrodes of a pair.

In another example, U.S. Pat. No. 5,891,179, Er et al, Method and Apparatus for Monitoring and Displaying Lead Impedance in Real-Time for an Implantable Medical Device, discloses a method and controller for displaying real-time graphical representations of variable lead impedance. Impedance values are calculated using Ohm's law or other related equations. Then the calculated impedance values are output to a graphic display for presentation thereby in graphical form or are output to a graphic printer, or both.

In another example, United States Patent Application Publication No. 2003/0114899, Samuelsson et al, Programming System for Medical Devices, discloses a method and controller for displaying graphical representations of a quantity influenced by the operation of a medical device. Such quantities may include information derived from tests and diagnostics, such as an electrode impedance test.

In another example, United States Patent Application Publication No. 2005/0033385, Peterson et al, Implantable Medical Device Programming Apparatus Having a Graphical User Interface, discloses graphical displays of the operation of a medical device, such as a test of a device lead. Results are organized according to the anatomical position of the lead, i.e., whether the lead is an atrial or ventricular lead, allowing the clinician to efficiently assess the functionally of all lead data by virtue of its grouping into precise anatomical categories.

In another example, U.S. Pat. No. 6,721,600, Jorgenson et al, Implantable Lead Functional Status Monitor and Method, discloses a system for obtaining trend data on the status of leads of an implantable medical device. The lead status measurement derives its data from various sources including lead impedance, non-physiologic sensed events, percentage of time the device is in mode switch, the results of capture management operation, sensed events, reversion paced counts, and refractory sense counts. The lead status measurement employs a set of weighted sum rules used by algorithms to process data from all of the above-mentioned sources to arrive at easily interpreted messages accessible to clinicians via an external programmer. Data from these sources identify lead conductor/connector interface issues and electrode/tissue interface issues indicative of lead-related mechanisms suggestive of impending or actual lead failure. The weights are "interpreted" for the user in the following manner either by indicating (1) lead-related parameters are all within range or operating normally; (2) one or more of the lead parameters are out-of-range and, thus, leads should be investigated; or (3) a number of lead parameters are out-of-range and a safety problem exists.

Messages to the user refer to three types of lead-related conditions: either lead/conductor/connector messages, lead insulation messages or biological interface messages. Examples of such messages include: (1) high impedance (>4000 ohms, 2× increase over reference, among others); (2) increase in threshold(s) above preset or programmed limit; and (3) reduction in R-wave and P-wave amplitude below preset or programmed limits.

Summary information from a variety of trend data is therefore presented for the use of a medical professional.

SUMMARY

But none of the above documents show, disclose or suggest a second impedance test run on electrodes that do not pass the first impedance test, varying active test parameters such as voltage, pulse width, frequency, current, power and electrode polarity from the first test to the second test. The present invention may conduct inter-electrode impedance measurements in ways fundamentally similar to the inventions disclosed above. Like much of the above cited documents, the controller may provide a range of impedance values considered normal, bounded on either end by values fixed for the test. In addition, a medical professional may specify which test parameters should be used and varied from test to test, and the range of impedance values considered normal for those chosen parameters. Inter-electrode impedance tests may also be conducted at voltage and current levels that are used by the device to deliver therapy in order to determine functionality at operation voltage levels. The controller may then provide recommendations specific to the therapy to be delivered.

In an embodiment, a controller for an implantable medical device has a plurality of electrodes, the implantable medical device being capable of delivering therapeutic stimulation to a patient through the plurality of electrodes. A control module, operatively coupled to the plurality of electrodes, is operable to conduct a plurality of measurements of impedance values creating a plurality of measured impedance values for a plurality of selected sets of individual ones of the plurality of electrodes based on a plurality of active parameters. The control module conducts the plurality of measurements of impedance values in a plurality of stages in which at least one of the plurality of active parameters is varied between individual ones of the plurality of stages.

In an embodiment, a system delivers therapeutic stimulation to a patient with an implantable medical device. A controller, operatively coupled to a plurality of electrodes, is operable to conduct a plurality of measurements of impedance values creating a plurality of measured impedance values for a plurality of selected sets of individual ones of the plurality of electrodes based on a plurality of active parameters. The control module conducts the plurality of measurements of impedance values in a plurality of stages in which at least one of the plurality of active parameters is varied between individual ones of the plurality of stages.

In an embodiment, one of the plurality of active parameters is a voltage, pulse width, frequency, current, power or electrode polarity.

In an embodiment, the controller compares the plurality of measurements of impedance values to a predetermined range.

In an embodiment, a subsequent one of the plurality of stages is conducted if a selected set of individual ones of the plurality of electrodes has a predetermined relationship with the predetermined range.

In an embodiment, the subsequent one of the plurality of stages is conducted if the selected set of individual ones of the plurality of electrodes has a measured impedance value outside of the predetermined range.

In an embodiment, a value of a stimulation parameter, e.g., voltage parameter, in the subsequent one of the plurality of stages is greater than a value of the stimulation parameter in a previous one of the plurality of stages.

In an embodiment, the value of the stimulation parameter does not exceed a maximum allowable value.

In an embodiment, the subsequent one of the plurality of stages is conducted if the selected set of individual ones of the plurality of electrodes has a measured impedance value inside of the predetermined range.

In an embodiment, a method delivers therapeutic stimulation to a patient using an implantable medical device having a plurality of electrodes. A first plurality of measurements of impedance values are obtained for a plurality of selected sets of individual ones of the plurality of electrodes using a plurality of active parameters. The measurements of impedance are compared with a predetermined range. A subsequent plurality of measurement of impedance values are automatically obtained for a plurality of selected sets of individual ones of the plurality of electrodes using a second plurality of active parameters.

In an embodiment, the second plurality of active parameters varies from the first plurality of active parameters.

In an embodiment, the active parameters are at least one of voltage, pulse width, frequency, current, power or electrode polarity.

In an embodiment, the subsequent plurality of measurements of impedance values are obtained for the selected sets of individual ones of the plurality of electrodes that are outside of a predetermined range.

In an embodiment, a stimulation parameter, e.g., a voltage parameter is increased in the subsequent plurality of measurements.

In an embodiment, the stimulation parameter does not exceed a maximum allowable value.

DETAILED DESCRIPTION

Figure 1:
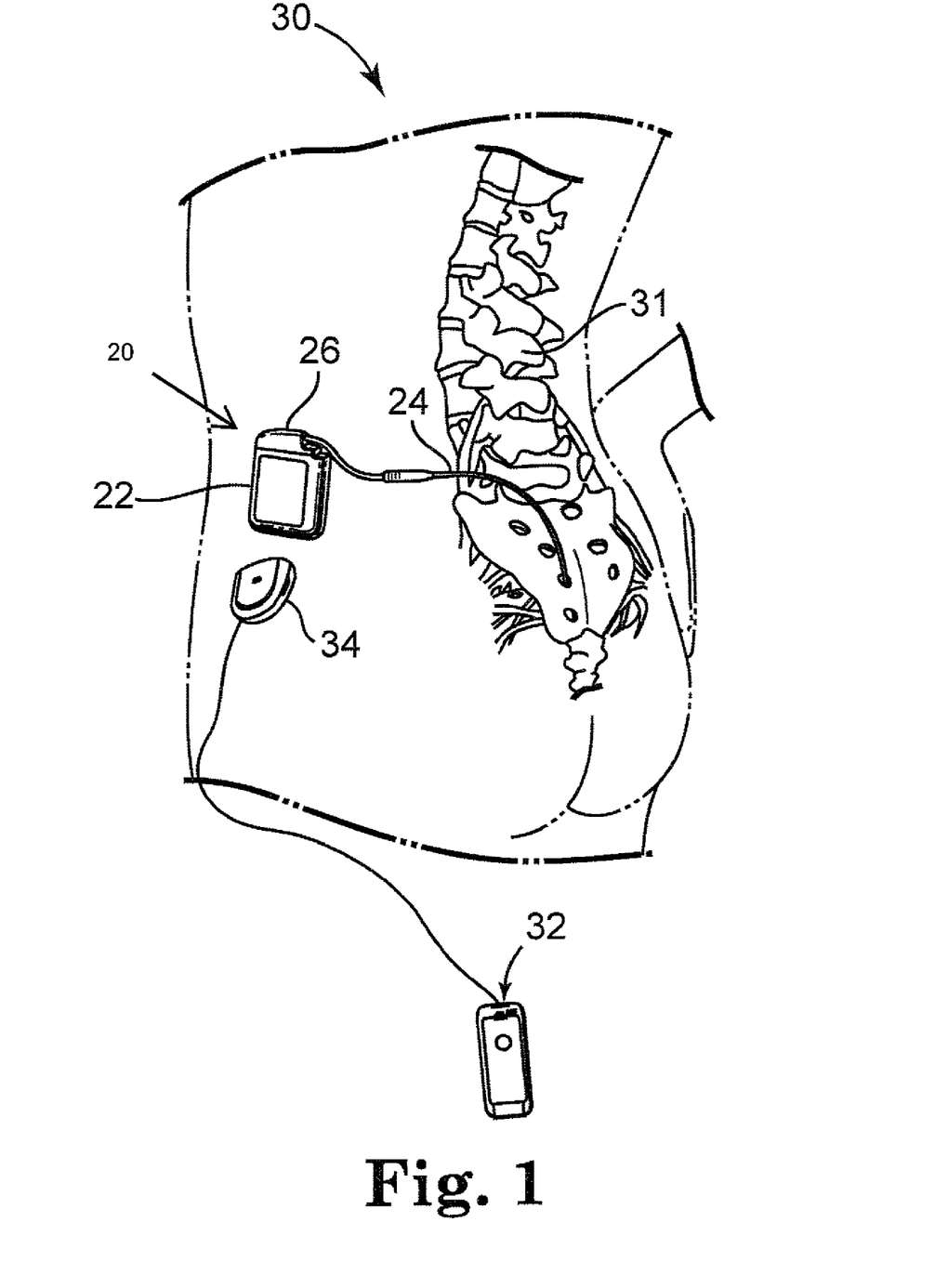
FIG. 1 shows an example of an implantable neurological stimulator implanted in the side of a patient, with electrodes positioned along the patient's spinal cord.

FIG. 1 shows the general environment of one rechargeable implantable medical device 20 embodiment. Implantable neurological stimulator 22 is shown, but other embodiments such as pacemakers and defibrillators and the like are also applicable. Implantable neurological stimulator 22 is implanted subcutaneously in side of patient 30. Lead 24 is operatively coupled to implantable neurological stimulator 22 at header 26. Lead 24 is positioned along spinal cord 31 of patient 30. Controller 32, which may be a physician programmer or patient programmer, may become transcutaneously coupled to implantable neurological stimulator 22 via an inductive communication link through the tissue of patient 30 when head 34 is placed in proximity to implantable neurological stimulator 22.

Figure 2:
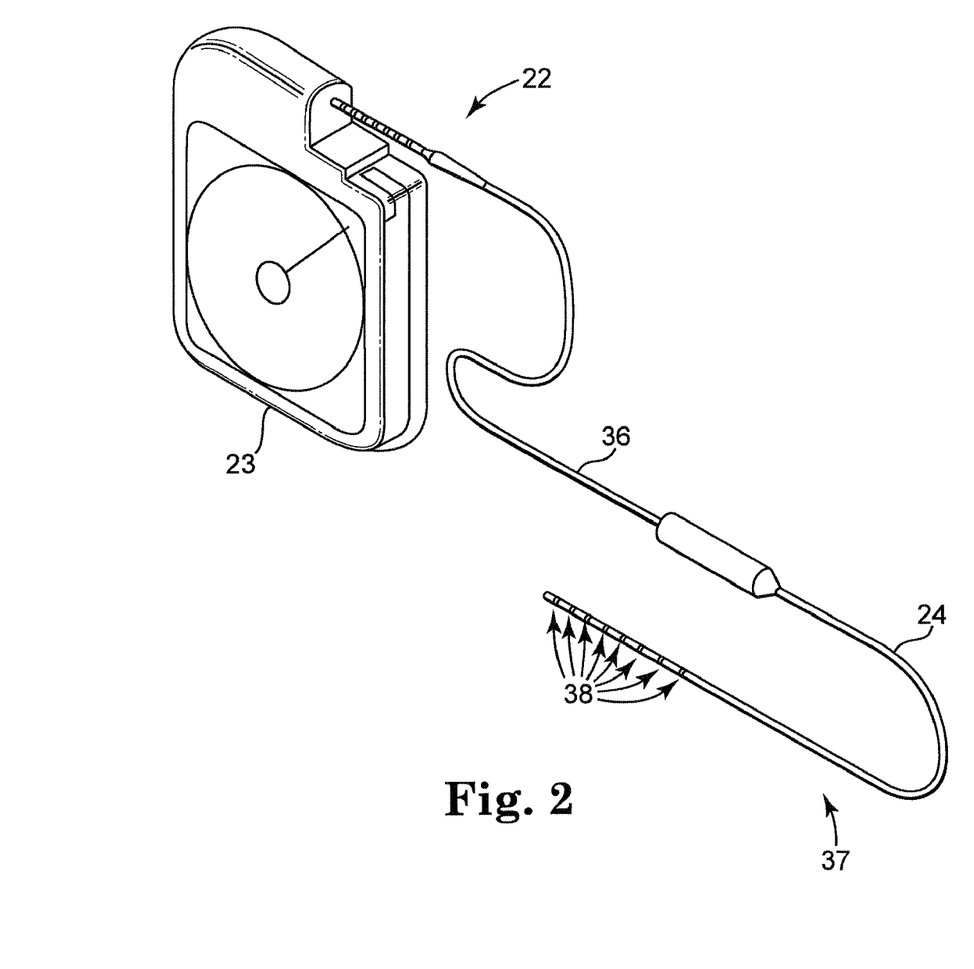
FIG. 2 shows an implantable neurological stimulator with a lead and lead extender and electrodes.
Figure 3:
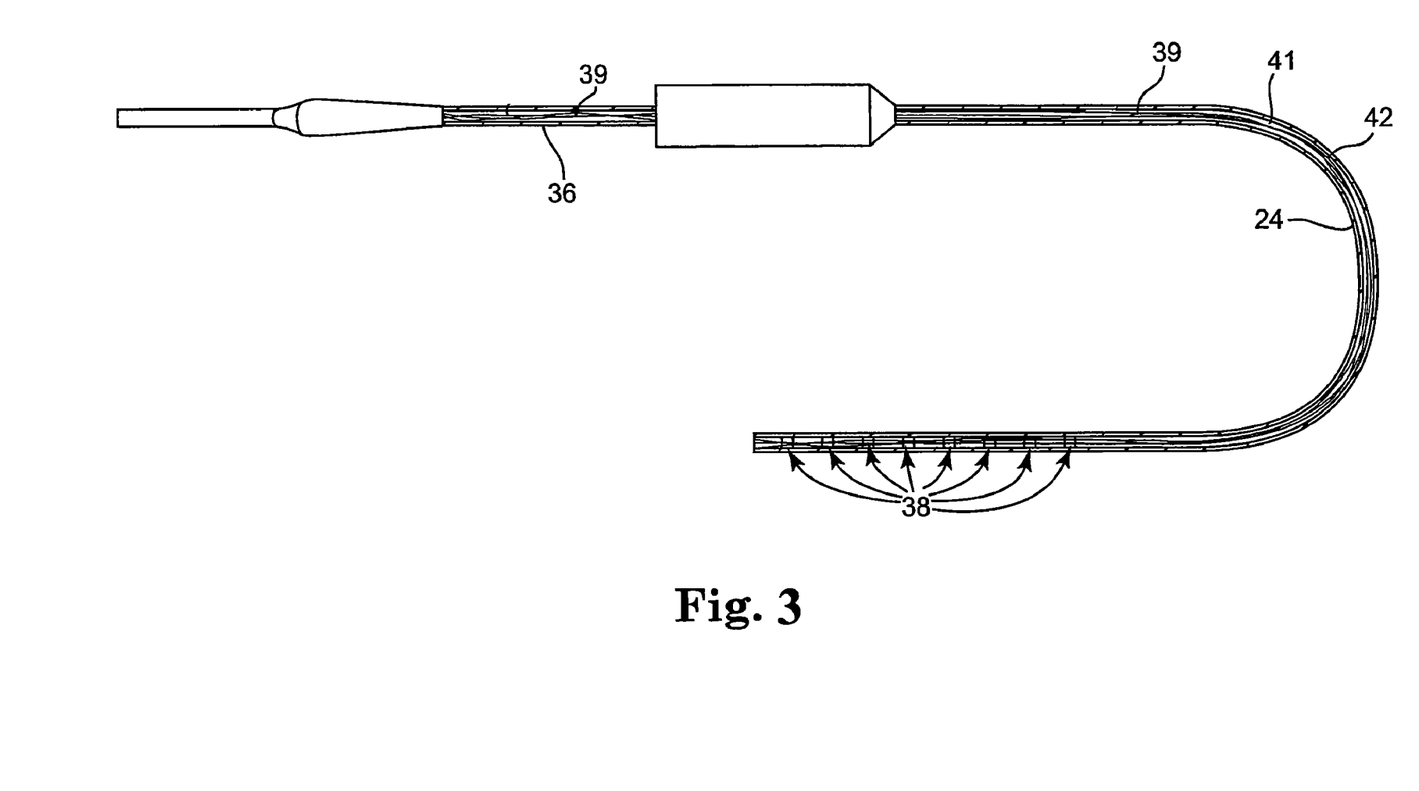
FIG. 3 shows a cutaway diagram of a lead with electrodes, and a lead extender, for an implantable medical device.

FIGS. 2 and 3 show a closer view of implantable neurological stimulator 22 and lead 24, operatively coupled by extender 36. Electrodes 38 are mounted on distal end 37 of lead 24. Electrodes 38 are comprised of a conductive material, in an embodiment, metal, that come into direct contact with tissue of patient 30. Electrodes 38 are operatively coupled with implantable neurological stimulator 22 via header 26 through wires 39 comprised of conductive material that pass through the interior 41 of lead 24 and are operatively coupled with conductive wires 39 in the interior 41 of extender 36.

Figure 4:
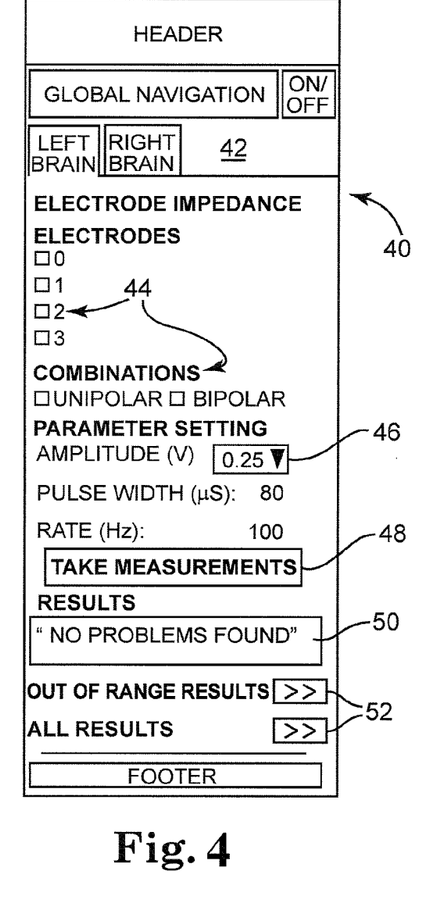
FIG. 4 shows a screen shot of a window for controlling an electrode impedance test of an implantable neurological stimulator.

FIG. 4 shows electrode impedance panel 40 for a controller or programmer for neurological stimulator 22, in this case a deep brain stimulator. Pick menus 42 allow selection of different leads 24 to test. Pick boxes 44 allow the medical professional or other user to select which electrodes 38 will be tested and whether those electrodes 38 will be tested in unipolar or bipolar configuration. Scroll menu 46 allows the medical professional or other user to set the value, e.g. voltage amplitude, and optionally, pulse width and frequency, at which the test will be conducted. In an embodiment, only active parameters, such as voltage amplitude, pulse width, frequency, current, power and electrode polarity may be set, while passive parameters, such as sense impedance, may not be set by the user or medical professional. Pressing button 48 begins the test according to the parameters that have been chosen on panel 40. After the test has completed a summary of the results is displayed in window 50, while buttons 52 give the medical professional or other user access to panel 60 (FIG. 5) that displays all results that were out of the predetermined range and to panel 80 (FIG. 6) that displays all results.

In a typical electrode impedance test, each electrode 38 will be tested both in unipolar mode and bipolar mode. Each electrode 38 in unipolar mode is paired up with an indifferent electrode, e.g., neurological stimulator case 23, and the impedance between each electrode 38 and indifferent electrode or implantable neurological stimulator case 23 is measured and stored. In addition, each electrode 38 in bipolar mode is paired up with every other electrode 38 and the impedance between each electrode 38 and every other electrode 38 is measured and stored. An exception may be that electrodes 38 that are located in different physiologic regions of the body, for instance the head or the chest, are never paired and tested.

It may be desirable to conduct electrode impedance testing at stimulation levels, e.g., voltage levels, as low as possible. Stimulation levels could also be current amplitude based. Using voltage as an example, maintaining the voltage levels relatively low may improve patient comfort during testing and save on battery life due to decreased power consumption during testing. However, due to a variety of physiologic reasons, including the impermeability of lipid formations on electrodes to relatively low voltage, electrode impedance testing conducted at low voltage levels may result in unrealistically high impedance measurements and resulting false-negative results, i.e., electrodes identified as being inoperable when, in fact, such an electrode actually is operable. Therefore, in an embodiment, while the initial electrode impedance measurements are conducted at relatively low voltage levels, in the event of a negative result the voltage level between the respective electrodes 38 may be progressively increased until either a positive measurement is obtained, or a maximum permissible level is reached and the impedance measurement is deemed to have failed. Increased voltage levels may be applied only to such electrode 38 pairs that do not pass the initial measurement and may only be applied until a positive result is obtained.

In an embodiment, only a set number of increases may be allowed. In an alternative embodiment, the number of increases is bounded by an allowable maximum voltage level. In an embodiment, the voltage initially defaults to 0.7 volts and then may increase to 1.5 volts and then may increase to 3.0 volts. Alternatively, the increase in voltage may occur in pre-set increments, e.g., by 0.25 volts, potentially determined, at least in part, by the type of therapy. Step size could also be a percentage, e.g., a five percent (5%) increase.

In further alternative embodiments, the parameter that may be increased, or altered in a more general embodiment, may be selected from a list including current, pulse width of the test signal, frequency of the signal, total power, and electrode polarity. In the case of power and current, the relationship to voltage is clear from Ohm's Law and the relationship between voltage, current and resistance/impedance to power. It is to be recognized and understood that complex impedances may be taken into account as well. In the case of pulse width and frequency, variations in the impedance between electrodes may have an impact on the waveform transmitted between electrodes 38. A comparison of the received waveform with the transmitted wave form based on analysis of frequency and pulse width may give an indication of the nature of the impedance between electrodes 38. For electrode polarity, by switching the polarity of one or more electrodes 38, more insight into the nature of the impedance between electrodes may be discerned by comparing the transmitted and received waveforms.

Data involving impedance measurements are potentially useful to a medical professional beyond the simple determination of passing or failing the test. In an embodiment, the medical professional may be provided with the results of each measurement in the event the initial impedance measurement is a failure in order to allow an assessment of electrodes that may be considered "weak" or potentially prone to failure in the future. However, the ultimate success or failure of the impedance measurement for the electrode 38 pair is determined based on a single positive measurement. Where a medical professional is concerned about failures at lower voltage levels, the medical professional may implement independent follow-up testing. In an alternative embodiment, an electrode 38 pair that had one or more failure before a passed test may be automatically tested again in order to verify that the pass result was not a false-positive.

It is also contemplated that instead of or in addition to changing or increasing a stimulation parameter from testing stage to testing stage, it is also contemplated that the electrode, electrodes or electrode set that is tested in each stage. As an example, only those electrodes that test out of range or test as performing poorly may be tested at an increased stimulation parameter in a subsequent stage.

Figure 5:
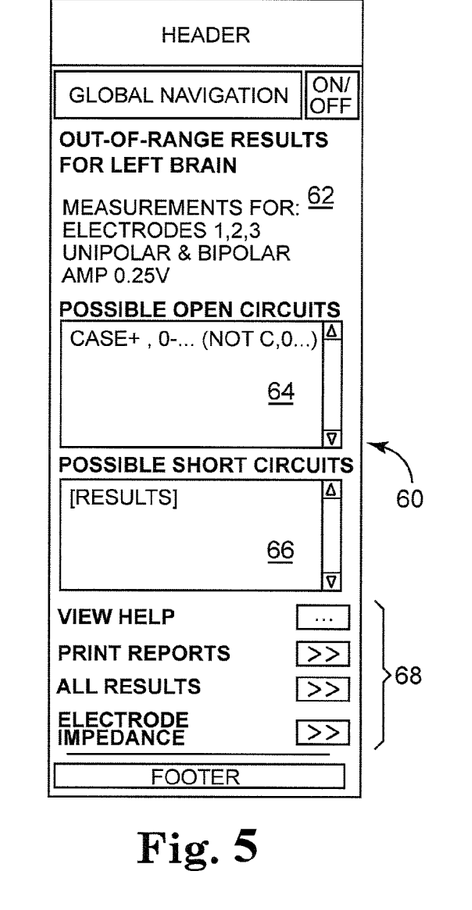
FIG. 5 shows a screen shot of a window for displaying out-of-range results of an electrode impedance test of an implantable neurological stimulator.

FIG. 5 shows out of range results panel 60 for displaying the results of testing initiated from electrode impedance panel 40. Text 62 at top of out of range results panel 60 informs the medical professional or other user what test the current results pertain to by displaying which electrodes 38 were tested, in which mode electrodes 38 were tested and at which voltage amplitude electrodes 38 were tested. Possible open circuits window 64 lists possible locations, e.g., all possible locations, of open circuits that cause faults of tested electrodes 38. Possible short circuits window 66 lists possible locations, e.g., all possible locations, of short circuits that cause faults. Buttons 68 provide access to all results panel 80 (FIG. 6) and electrode impedance panel 40, as well as a print command to print the data displayed on out of range results panel 60.

Open circuits are typically detectable when all measured impedance values for one electrode 38 are higher than the allowable maximum value. For instance, if all impedance values involving electrode (38) number two exceed the maximum value and all impedance values not involving electrode 38 number two are within the allowable value, the controller could conclude that an open circuit existed on the path along which electrode (38) number two was operatively coupled with implantable neurological stimulator 22. Similarly, if all measured impedance values pertaining to electrodes (38) number two and six exceeded the maximum value and all impedance values not involving electrodes (38) number two and six are within the allowable values, the controller could conclude that both electrodes (38) number two and six were open.

By contrast, short circuits are typically detectable when all measured impedance values involving those two electrodes (38) are lower than average and the measured impedance value between the two electrodes 38 is below the minimum allowable value. For instance, if the average impedance between electrodes (38) is five hundred ohms, but between electrodes (38) four and five, and four and six, in bipolar mode, and electrodes (38) five and case 23 and six and case 23 were all four hundred ohms, and the impedance between electrodes 38 five and six was below the allowable minimum value, controller 32 (FIG. 7) could conclude that there is a short circuit between electrodes (38) five and six. Such short circuits can occur, among other reasons, because the electrodes 38 in question are physically touching, or insulation 42 between wires 39 operatively coupling electrodes 38 with implantable neurological stimulator 22 have frayed.

Occasionally, the results of testing may provide ambiguous results. For instance, if the impedance between electrodes (38) zero and two, three and two and between electrode (38) two and case 23 are all greater than the maximum allowable value, but the impedance between electrodes (38) one and two is within the allowable range, then it might not be clear what is the underlying cause of the issue. Controller 32 could return a message indicating that out of range values had been detected, but could be unable to offer definitive prescriptive guidance.

Figure 6:
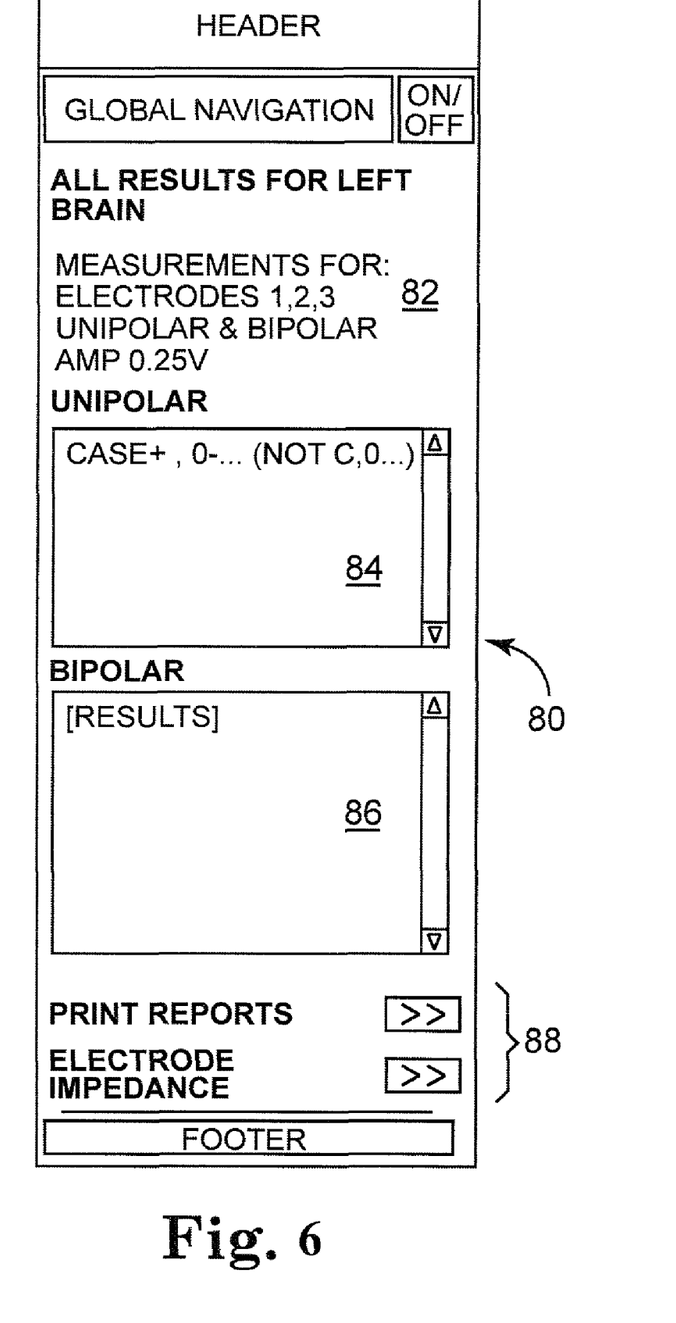
FIG. 6 shows a screen shot of a window for displaying results of an electrode impedance test of an implantable neurological stimulator.

FIG. 6 shows all results panel 80, for displaying all results of testing initiated from electrode impedance panel 40, regardless of whether testing resulted in an indication of failure or failures or not. Text 82 at the top of all results panel 80 informs the medical professional or other user to what test the current results pertain by displaying which electrodes 38 were tested, in which mode electrodes 38 were tested and at which voltage amplitude electrodes 38 were tested. Results are displayed in one of two windows 84, 86 depending on if the test mode was unipolar 84 or bipolar 86. Buttons 88 provide access to electrode impedance panel 40 and a print command.

Figure 7:
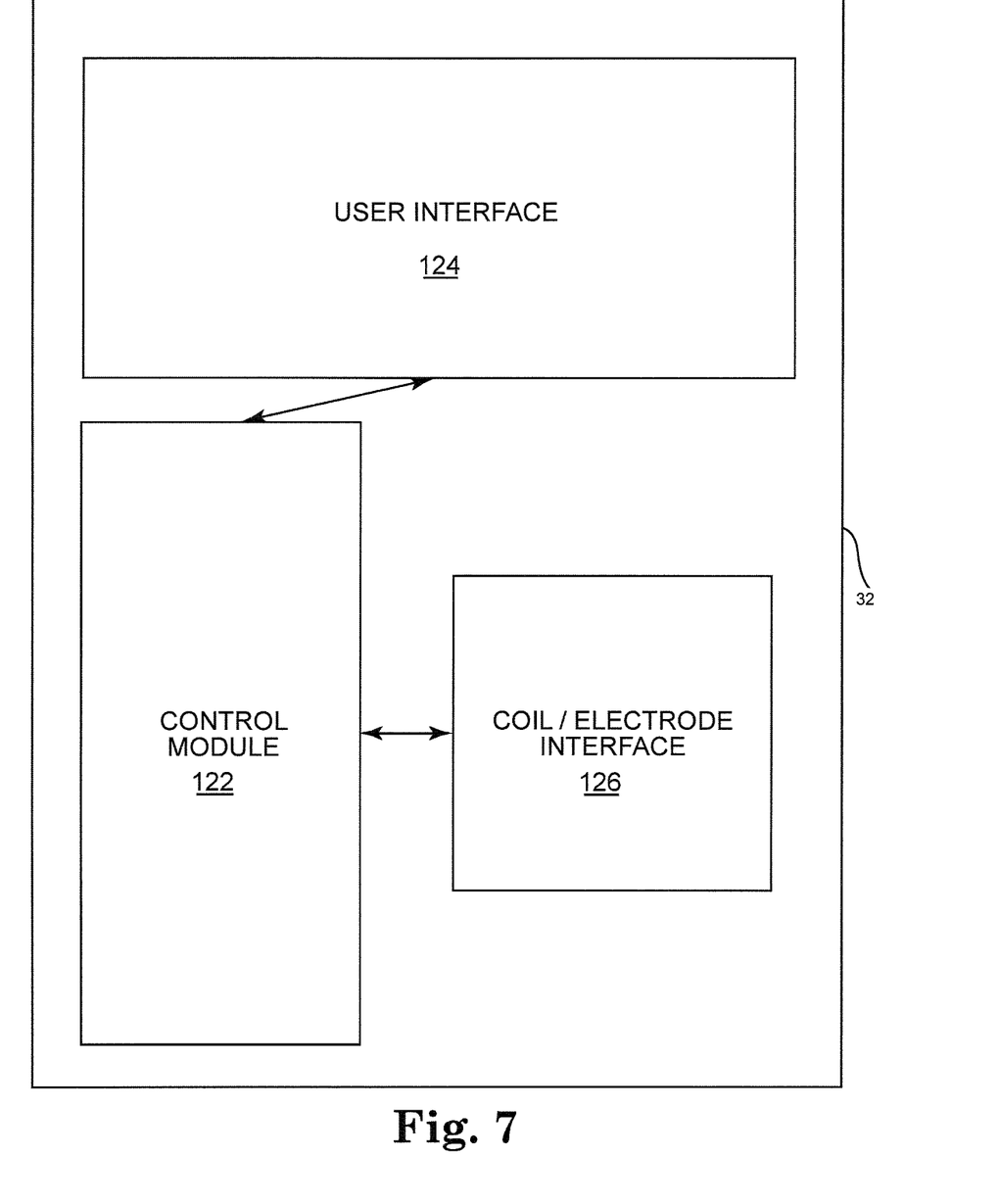
FIG. 7 shows a block diagram of a controller for an implantable medical device.

FIG. 7 shows a block diagram of the functional blocks of controller 32. Control module 122 comprises a variety of off the shelf electronic components commonly found in a variety of commercial applications, such as personal computers. These electronic components include: a microprocessor, RAM, ROM and hard disks. These off the shelf components are integrated into control module 122 and additional operational features are added via custom electronics. These custom electronics are comprised of off the shelf integrated circuits and discrete components, and programmable components, such as FPGAs and DSPs, and custom integrated circuits and PCBs.

Figure 8:
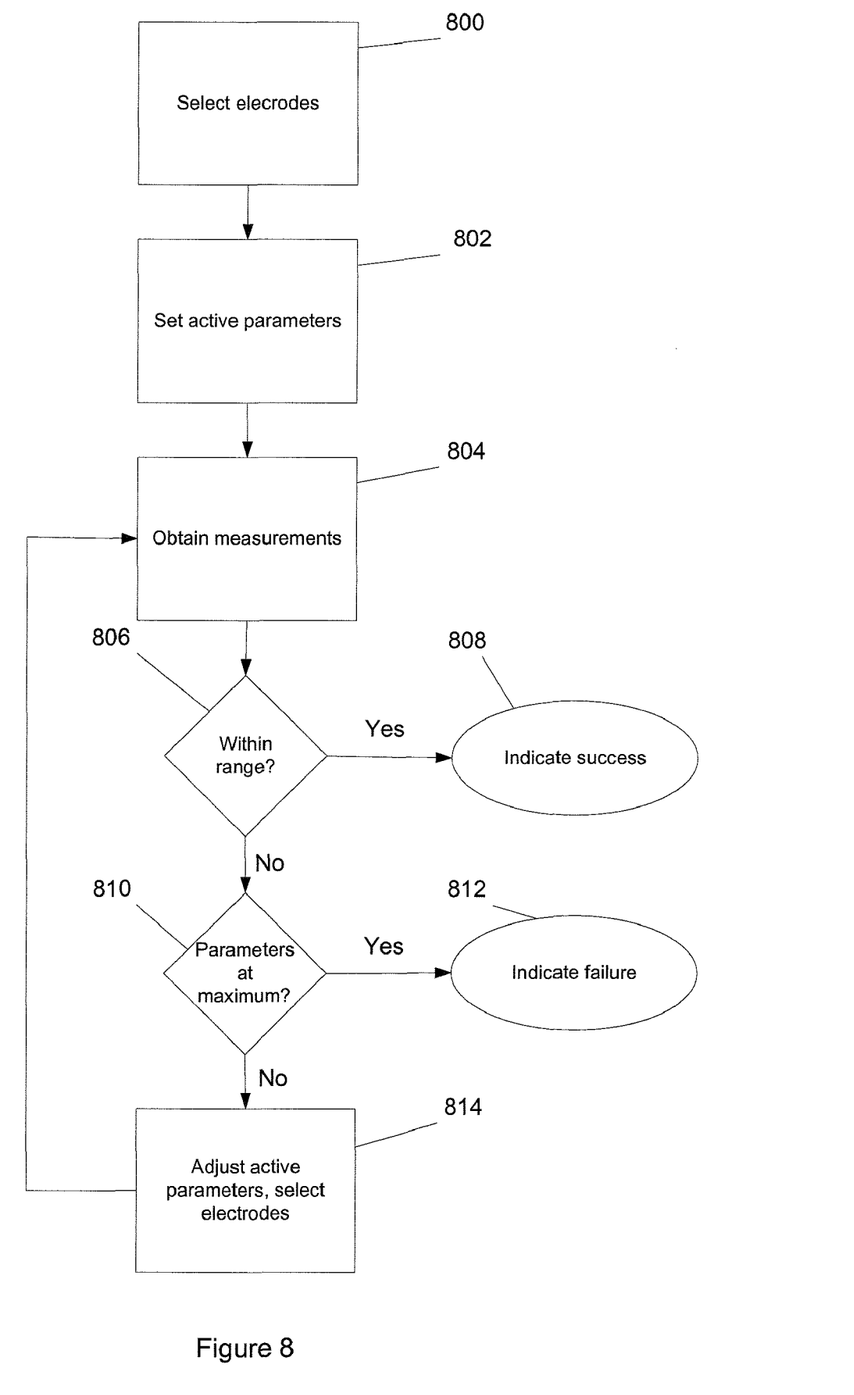
FIG. 8 is a flow chart for conducting a therapy impedance measurement for an implantable medical device.

FIG. 8 is a flow chart for measuring impedance electrodes 38 when delivering stimulation. It may be desirable to verify that the electrodes 38 will deliver therapy as anticipated. Sometimes lipids form on electrodes 38 and while voltage levels below a threshold value will not penetrate the lipid layer, thereby suggesting high impedance, voltage levels higher than the threshold value will pass through, thereby suggesting acceptable impedance. The allowable range of impedance values may vary depending on the specific characteristics of the therapy to be delivered.

To initialize the electrode impedance test, a user may utilize electrode impedance panel 40 to select (800) which electrodes 38 will be tested, and then to select (802) which active parameters, such as voltage amplitude, pulse width, frequency, current, power and electrode polarity. Once the active parameters have been selected, the user may initiate the electrode impedance test using button 48, and the system obtains (804) the corresponding measurements according to methods known in the art.

After obtaining the measurements, control module 32 or implantable neurological stimulator 22 may compare (806) the measured impedance against a predetermined range indicative of an acceptable measured impedance level. An acceptable impedance value may be influenced, especially at the lower bound, by many factors including the short circuit impedance of leads, extensions and device electronics and the type of tissue being stimulated. In an embodiment, an acceptable lower bound is fifty (50) ohms. In another embodiment, an acceptable lower bound is two hundred fifty (250) ohms. In an embodiment, an acceptable impedance value at the upper bound is 2,000 ohms for a uni-polar configuration and 4,000 ohms for a bi-polar configuration. In alternative embodiments, the acceptable range may be set by a medical professional or by the device dependent on the characteristics of patient 30, implantable neurological stimulator 22 or electrodes 38. In an embodiment, if all of the measured results fall (808) within the predetermined acceptable range, controller 32 may indicate a successful test in window 50 and in all results panel 80.

However, if any of the measured results fall outside of the predetermined range, it may be determined (810) whether the active parameters at which the measurements were conducted are already at a predetermined allowable maximum. In such a case, to increase the active parameters further may place the patient at risk of suffering discomfort or injury. Thus, if the active parameters are at a predetermined maximum such that one may not safely or comfortably proceed further, an indication of an unsuccessful test may be displayed (812) in window 50, with further information displayed in out of range results panel 60 and all results panel 80.

If, however, the active parameters do not exceed the predetermined maximum, some or all of the active parameters may be automatically increased (814) incrementally such that they do not exceed the predetermined maximum. In addition, if some combinations of electrodes 38 passed in previous impedance testing (804), a flag may be set indicating that those electrodes 38 had already shown acceptable measured results, while the electrode 38 combinations that had not previously passed may be selected for retesting. Then, once the active parameters have been modified and the electrodes 38 selected, a new set of impedance measurements may be obtained (804). This process may be repeated either until all impedance measurements give results within the predetermined range, or until the active parameters reach the predetermined maximum.

Alternatively, a predetermined range may be established which is indicative of a range of impedances in which retesting of electrodes, perhaps at an increased voltage, may be desirable. For example, a range may be established that represents impedances which are higher than would clearly indicate an acceptable level for an operational electrode but which is not so high as to be unreasonable for retest. Electrodes with impedances within such range may be selected for retest with the expectation that one or more of such retested electrodes could possibly fall within acceptable limits, for example, if the retest were conducted at a higher voltage. Electrodes with impedances higher than such range may, optionally, be excluded from retesting, possibly because such a high impedance might not reasonably be expected to decrease enough to be considered acceptable in retest. Hence, retest of such an electrodes could be eliminated.

While much of foregoing discussion has involved the increase in stimulation parameter or parameters from stage to stage, it is to be recognized and understood that a stimulation parameter, e.g., voltage amplitude, may be decreased from stage to stage. For example, a goal may be to move from less accurate stimulation parameters to more accurate stimulation parameters. A stimulation parameter may be decreased from one stage to the next stage in order determine or calibrate a lower stimulation parameter or bound for testing. A decrease in a stimulation parameter or parameters may be helpful in the establishment or re-establishment of a parameter calibration.

In an embodiment, after setting (800) the electrodes 38 to be tested and selecting (802) the starting values for the active parameters, no further user input is required in order to do a complete series of impedance measurements. In a further embodiment, the user does not need to do anything other than initiate testing via button 48, with either controller 32 or implantable neurological stimulator 22 setting (800) the electrodes 38 to be tested, in an embodiment all of the electrodes, and setting (802) the initial values for the active parameters.

Thus, embodiments of the controller for multi-stage testing of electrodes of implantable medical device, system and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A controller for an implantable medical device having a plurality of electrodes, said implantable medical device being capable of delivering therapeutic stimulation to a patient through said plurality of electrodes, comprising:
a control module operatively coupled to said plurality of electrodes;
said control module configured to conduct a plurality of measurements of impedance values in a plurality of stages;
said control module being configured to conduct, in a first one of said plurality of stages, a measurement of an impedance value for a first group of a plurality of selected sets of said plurality of electrodes;
said control module being configured to conduct, in a second one of said plurality of stages, a measurement of said impedance value for a second group of at least one selected set of said plurality of electrodes;
wherein said first group of said plurality of selected sets is different from said second group of at least one selected set; and
wherein at least one of a plurality of active parameters is varied between individual ones of said plurality of stages, and wherein said at least one of said plurality of active parameters comprises at least one of voltage, pulse width, frequency, current, power and electrode polarity.

2. The controller as in claim 1 wherein said controller compares said plurality of measurements of impedance values to a predetermined range.

3. The controller as in claim 2 wherein a said second one of said plurality of stages is conducted if a selected set of said first group of said plurality of selected sets of said plurality of electrodes has a predetermined relationship with said predetermined range.

4. The controller as in claim 2 wherein said first group of said plurality of selected sets and said second group of at least one selected set are varied between said first stage and said second stage.

5. The controller as in claim 3 wherein said second one of said plurality of stages is conducted if said selected set of said first group of said plurality of selected sets of said plurality of electrodes has a measured impedance value outside of said predetermined range.

6. The controller as in claim 3 wherein said second one of said plurality of stages is conducted if said selected set of said first group of said plurality of selected sets of individual ones of said plurality of electrodes has a measured impedance value inside of said predetermined range.

7. The controller as in claim 5 wherein a value of a stimulation parameter in said second one of said plurality of stages is greater than a value of said stimulation parameter in said first stage.

8. The controller as in claim 7 wherein said value of said stimulation parameter does not exceed a maximum allowable value.

9. The controller as in claim 8 wherein said stimulation parameter is voltage and wherein said maximum allowable value is a maximum allowable voltage.

10. The controller as in claim 8 wherein said stimulation parameter is current and wherein said maximum allowable value is a maximum allowable current.

11. The controller as in claim 8 wherein said stimulation parameter is pulse width and wherein said maximum allowable value is a maximum allowable pulse width.

12. The controller as in claim 1 wherein said first group of said plurality of selected sets and said second group of at least one selected set are varied between said first stage and said second stage.

13. The controller as in claim 12 wherein said first group and said second group are varied dependent, at least in part, upon a comparison of said plurality of measurements to said predetermined range.

14. The controller as in claim 13 wherein said comparison of said plurality of measurements results in at least one of said plurality of electrodes is outside of said predetermined range.

15. A system for delivering therapeutic stimulation to a patient, comprising:
an implantable medical device having a plurality of electrodes; and
a controller, comprising:
a control module operatively coupled to said plurality of electrodes; and said control module configured to conduct a plurality of measurements of impedance values in a plurality of stages;

said control module being configured to conduct, in a first one of said plurality of stages, a measurement of an impedance value for a first group of a plurality of selected sets of said plurality of electrodes;

said control module being configured to conduct, in a second one of said plurality of stages, a measurement of said impedance value for a second group of at least one selected set of said plurality of electrodes;

wherein said first group of said plurality of selected sets is different from said second group of at least one selected set; and wherein at least one of a plurality of active parameters is varied between individual ones of said plurality of stages, wherein at least one of said plurality of active parameters comprises at least one of voltage, pulse width, frequency, current, power and electrode polarity.

16. The system as in claim 15 wherein said controller compares said plurality of measurements of impedance values to a predetermined range.

17. The system as in claim 16 wherein said second one of said plurality of stages is conducted if a selected set of said first group of said plurality of selected sets of said plurality of electrodes has a predetermined relationship with said predetermined range.

18. The system as in claim 17 wherein said second one of said plurality of stages is conducted if said selected set of said first group of said plurality of selected sets of said plurality of electrodes has a measured impedance value outside of said predetermined range.

19. The system as in claim 17 wherein said second one of said plurality of stages is conducted if said selected set said first group of said plurality of selected sets of individual ones of said plurality of electrodes has a measured impedance value inside of said predetermined range.

20. The system as in claim 18 wherein a value of a stimulation parameter in said second one of said plurality of stages is greater than a value of said stimulation parameter in said first stage.

21. The system as in claim 20 wherein said value of said stimulation parameter does not exceed a maximum allowable value.

22. The system as in claim 20 wherein said stimulation parameter is voltage and wherein said maximum allowable value is a maximum allowable voltage.

23. The system as in claim 20 wherein said stimulation parameter is current and wherein said maximum allowable value is a maximum allowable current.

24. The system as in claim 20 wherein said stimulation parameter is pulse width and wherein said maximum allowable value is a maximum allowable pulse width.

25. A method for delivering therapeutic stimulation to a patient using an implantable medical device having a plurality of electrodes, comprising the steps of:

obtaining a first plurality of measurements of impedance values for a first group of a plurality of selected sets of individual ones of said plurality of electrodes using a plurality of active parameters; then comparing said measurements of impedance with a predetermined range; and then automatically obtaining a subsequent plurality of measurements of impedance values for a second group of at least one selected set of individual ones of said plurality of electrodes different from said first group of said plurality of selected sets using a second plurality of active parameters, wherein said second plurality of active parameters varies from said first plurality of active parameters; and wherein said plurality of active parameters comprises at least one of voltage, pulse width, frequency, current, power and electrode polarity.

26. The method as in claim 25 wherein a selected set of said second group of said at least one selected set of individual ones of said plurality of electrodes is one of said plurality of selected sets which is outside of a said predetermined range.

27. The method as in claim 25 wherein a stimulation parameter is increased in said subsequent plurality of measurements.

28. The method as in claim 27 wherein said stimulation parameter does not exceed a maximum allowable value.

* * * * *